United States Patent
Macoviak et al.

(10) Patent No.: US 6,669,674 B1
(45) Date of Patent: Dec. 30, 2003

(54) INTRODUCER AND PERFUSION CANNULA

(75) Inventors: John A. Macoviak, La Jolla, CA (US); Wilfred J. Samson, Saratoga, CA (US); Lynn M. Thompson, Palo Alto, CA (US); James J. Leary, Sunnyvale, CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/566,859

(22) Filed: May 8, 2000

Related U.S. Application Data

(62) Division of application No. 09/158,407, filed on Sep. 22, 1998, now Pat. No. 6,099,506.
(60) Provisional application No. 60/059,946, filed on Sep. 26, 1997.

(51) Int. Cl.[7] .............................................. A61M 25/00
(52) U.S. Cl. ........................................ 604/264; 604/104
(58) Field of Search .................... 604/103.04, 173–175, 604/264, 523, 539, 533, 284, 43, 178, 158, 164.01, 167.01, 256, 165.01, 104; 600/213, 167, 198

(56) References Cited

U.S. PATENT DOCUMENTS

| | | | |
|---|---|---|---|
| 4,016,884 A | * 4/1977 | Kwan-Gett | 604/175 |
| 4,306,545 A | * 12/1981 | Ivan et al. | 128/887 |
| 4,411,655 A | 10/1983 | Schreck | |
| 4,527,549 A | 7/1985 | Gabbay | |
| 4,639,247 A | * 1/1987 | Bokros | 604/175 |
| 4,808,163 A | 2/1989 | Laub | |
| 5,190,528 A | 3/1993 | Fonger et al. | |
| 5,216,032 A | 6/1993 | Manning | |
| 5,250,038 A | 10/1993 | Melker et al. | |
| 5,254,097 A | 10/1993 | Schock | |
| 5,269,772 A | * 12/1993 | Wilk | 604/284 |
| 5,273,534 A | * 12/1993 | Knoepfler | 604/97.02 |

(List continued on next page.)

FOREIGN PATENT DOCUMENTS

| | | | |
|---|---|---|---|
| EP | 86201487 | 8/1986 | A61M/25/00 |
| EP | 0 209 070 A2 | 1/1987 | A61M/1/10 |
| WO | WO 93/25265 | 12/1993 | A61M/29/00 |
| WO | WO 96/40347 | 12/1996 | A61M/29/00 |
| WO | WO 97/37581 | 10/1997 | |
| WO | WO 99/04848 | 7/1998 | |

Primary Examiner—Manuel Mendez
Assistant Examiner—Cris L. Rodriguez
(74) Attorney, Agent, or Firm—Fulwider Patton Lee & Utecht, LLP

(57) ABSTRACT

The present invention discloses a multi-access cannula for use in a variety of surgical procedures, particularly for use in the course of performing conventional open-chest and peripheral access cardiopulmonary bypass (CPB). The multi-access cannula is capable of being inserted through a single puncture site with a percutaneous tip. At the appropriate depth of insertion, a closure seal may be engaged at the point of entry to secure the positioning of the cannula and prevent leakage of blood from the incision. Once the cannula is at the appropriate position the cannula provides a multiplicity of procedural options for the surgeon. For example, when approaching through the ascending aorta, the multi-access cannula enables the simultaneous passage of various fluids and multiple catheters or instruments in opposing directions within the lumen of the aortic arch through a single insertion site.

36 Claims, 6 Drawing Sheets

U.S. PATENT DOCUMENTS

| | | | |
|---|---|---|---|
| 5,308,320 A | | 5/1994 | Safar et al. |
| 5,312,344 A | | 5/1994 | Grinfield et al. |
| 5,324,260 A | | 6/1994 | O'Neill |
| 5,330,433 A | | 7/1994 | Fonger |
| 5,334,142 A | | 8/1994 | Paradis |
| 5,342,295 A | | 8/1994 | Imran |
| 5,346,471 A | * | 9/1994 | Raulerson .................. 604/43 |
| 5,354,288 A | | 10/1994 | Cosgrove et al. |
| 5,370,640 A | | 12/1994 | Kolff |
| 5,383,854 A | | 1/1995 | Safar et al. |
| 5,413,558 A | | 5/1995 | Paradis |
| 5,421,825 A | * | 6/1995 | Farcot ..................... 604/44 |
| 5,425,724 A | | 6/1995 | Akins |
| 5,433,700 A | | 7/1995 | Peters |
| 5,437,633 A | | 8/1995 | Manning |
| 5,451,207 A | | 9/1995 | Yock |
| 5,458,574 A | | 10/1995 | Machold et al. |
| 5,476,453 A | * | 12/1995 | Mehta ..................... 604/532 |
| 5,478,309 A | | 12/1995 | Sweezer et al. |
| 5,509,908 A | | 4/1996 | Hillstead et al. |
| 5,542,936 A | | 8/1996 | Razi |
| 5,562,606 A | | 10/1996 | Huybregts |
| 5,584,803 A | | 12/1996 | Stevens et al. |
| 5,591,128 A | | 1/1997 | Sithole |
| 5,599,304 A | * | 2/1997 | Shaari .................. 604/94.01 |
| 5,599,329 A | | 2/1997 | Gabbay |
| 5,607,462 A | | 3/1997 | Imran |
| 5,613,946 A | | 3/1997 | McKeever |
| 5,616,137 A | | 4/1997 | Lindsay |
| 5,678,570 A | | 10/1997 | Manning |
| 5,683,363 A | | 11/1997 | McKeever |
| 5,685,865 A | | 11/1997 | Cosgrove et al. |
| 5,695,457 A | * | 12/1997 | St. Goar .................. 604/4.01 |
| 5,700,243 A | | 12/1997 | Narciso, Jr. |
| 5,702,368 A | | 12/1997 | Stevens et al. |
| 5,716,318 A | | 2/1998 | Manning |
| 5,722,426 A | | 3/1998 | Kolff |
| 5,725,496 A | | 3/1998 | Peters |
| 5,752,938 A | | 5/1998 | Flatland et al. |
| 5,755,687 A | | 5/1998 | Donlon et al. |
| 5,755,784 A | | 5/1998 | Jarvik |
| 5,759,170 A | | 6/1998 | Peters |
| 5,766,151 A | * | 6/1998 | Valley et al. .......... 604/103.07 |
| 5,769,812 A | | 6/1998 | Stevens et al. |
| 5,769,828 A | | 6/1998 | Jonkman |
| 5,776,190 A | | 7/1998 | Jarvik |
| 5,792,094 A | | 8/1998 | Stevens et al. |
| 5,795,325 A | | 8/1998 | Valley et al. |
| 5,800,375 A | | 9/1998 | Sweezer et al. |
| 5,810,757 A | | 9/1998 | Sweezer et al. |
| 5,814,016 A | | 9/1998 | Valley et al. |
| 5,820,593 A | | 10/1998 | Safar et al. |
| 5,830,191 A | | 11/1998 | Hildwein et al. |
| 5,830,232 A | * | 11/1998 | Hasson ..................... 606/213 |
| 6,095,997 A | * | 8/2000 | French et al. .................. 604/9 |
| 6,217,555 B1 | * | 4/2001 | Hart et al. ............. 604/167.01 |
| 6,319,246 B1 | * | 11/2001 | de la Torre et al. ............ 606/1 |

* cited by examiner

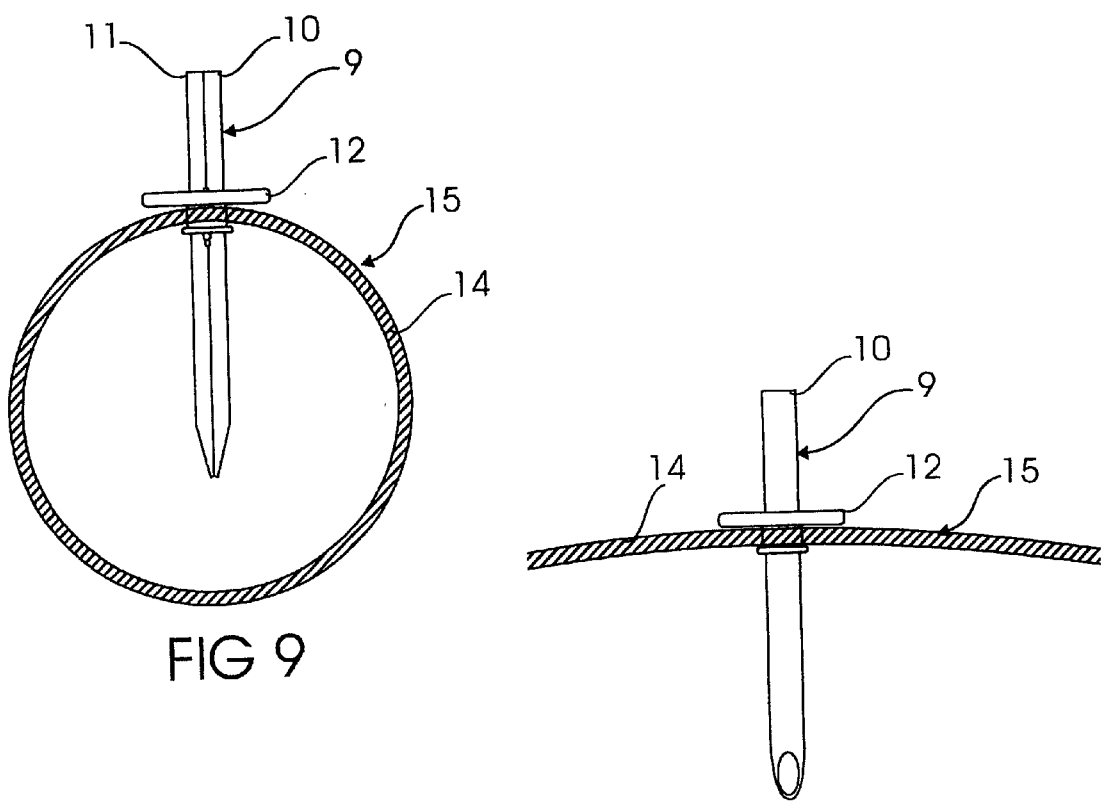
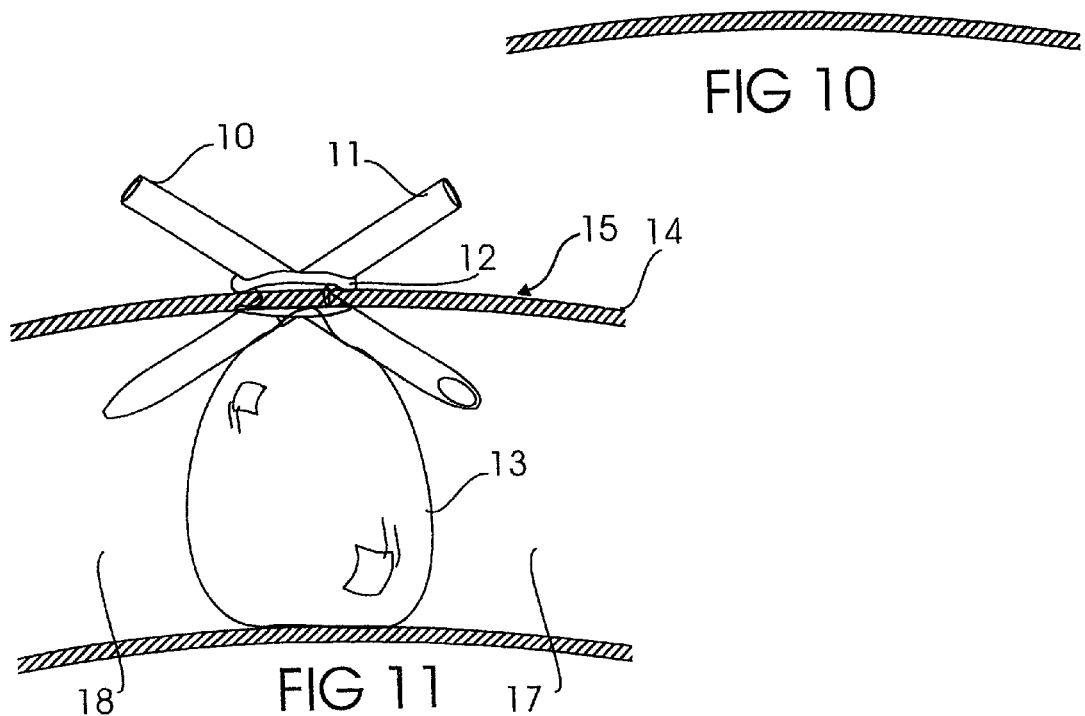

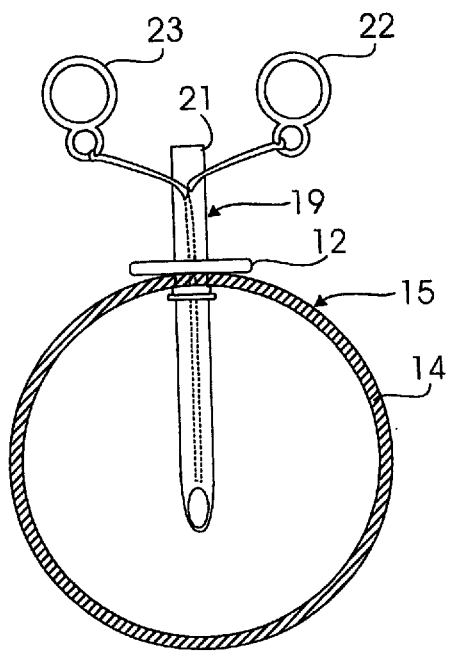
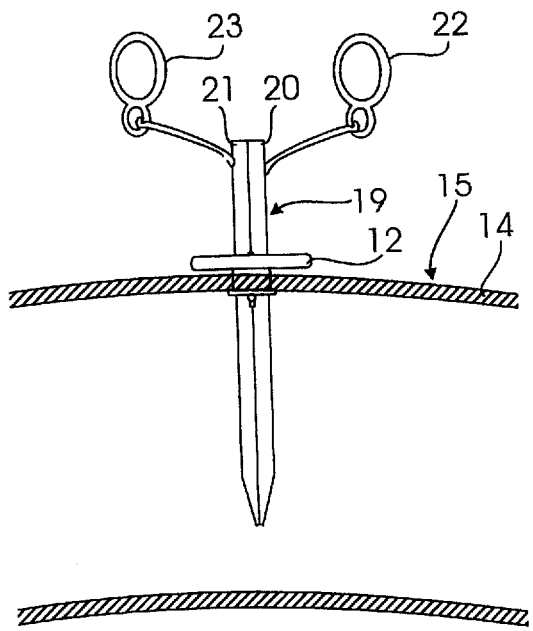
FIG 12
FIG 13
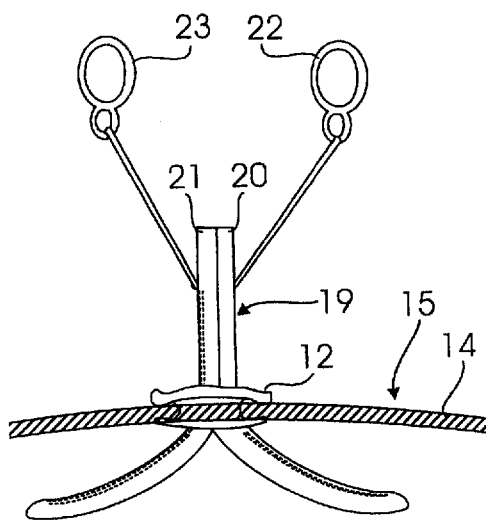
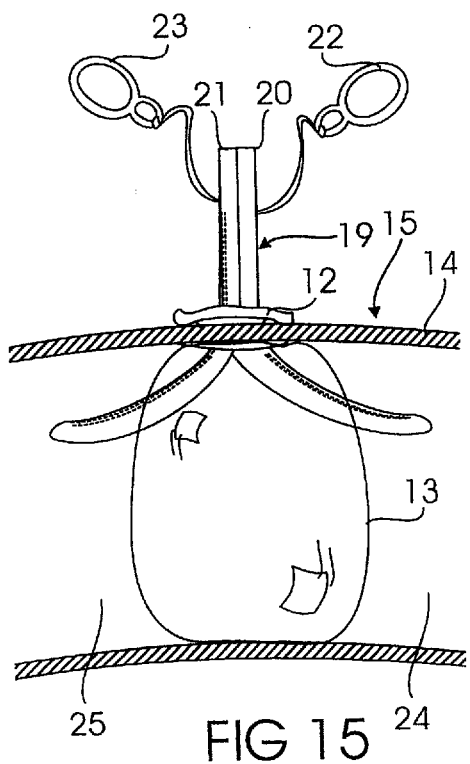
FIG 14
FIG 15

INTRODUCER AND PERFUSION CANNULA

CROSS REFERENCE TO OTHER APPLICATIONS

This application is a division of Ser. No. 09/158,407 filed Sep. 22, 1998 which is now a U.S. Pat. No. 6,099,506.

This application claims the benefit of U.S. Provisional Application No. 60/059,946, filed Sep. 26, 1997, the specification of which is hereby incorporated by reference in its entirety.

FIELD OF THE INVENTION

This invention relates to a cannula or catheter device that is capable of multi-access and multidirectional flow for use in providing total cardiopulmonary bypass support and isolation of the heart during traditional open chest surgery as well as minimally invasive surgical techniques.

BACKGROUND OF THE INVENTION

This invention relates to improvements in devices used for cardiovascular, pulmonary and neurosurgical procedures where the patient is placed on cardiopulmonary bypass. More specifically, this invention relates to an introducer and perfusion cannula device that provides a single insertion site where multiple catheters may be inserted in order to provide multidirectional flow and access.

Although there are existing introducers or perfusion cannulas that offer access for introduction of catheters or cannulas into a patient's aorta or other vascular access sites, none offer the benefits of the current invention. U.S. Pat. No. 5,478,309 (Sweezer) describes an aortic perfusion cannula offering access for a catheter device through an aortic insertion site. However, the device described by Sweezer does not provide access for multiple catheter devices, nor does it provide multidirectional flow. In addition, U.S. Pat. No. 5,254,097 (Schock) describes a device that allows for insertion of a catheter device, e.g. an intra-aortic balloon pump, through a femoral artery perfusion cannula, however this device does not provide access for multiple catheter devices, nor does it provide multidirectional flow. By providing access for multiple catheter devices and multidirectional flow through a single insertion site, the present invention facilitates segmentation of a patient's aorta for selective perfusion and it allows repositioning and exchanging of catheter devices without additional trauma to the insertion site.

Furthermore, the present invention offers the benefit of a sealing mechanism that is capable preventing blood flow outside of a vessel after insertion. By providing a sealing mechanism of this type, a surgeon is able to secure the cannula in a fixed position after insertion without having to be concerned with cannula movement or blood loss through the insertion site. In addition, the sealing device allows insertion of multiple catheter devices and repositioning or exchanging of catheter devices without additional trauma to the insertion site.

In a further aspect, the invention provides for a flow control regulator that may take the form of an occlusion balloon. By incorporating such a device into the present cannula, segmentation of the aorta is possible and because of the position of the occlusion balloon on the cannula shaft multidirectional flow is still accomplished.

SUMMARY OF THE INVENTION

The present invention provides a multi-access cannula for use in a variety of surgical procedures, particularly for use in the course of performing conventional open-chest and peripheral access cardiopulmonary bypass (CPB). In such procedures, the multi-access cannula facilitates insertion of multiple cannulas or catheter devices through a single puncture site. At the appropriate depth of insertion, a closure seal may be engaged at the point of entry to secure the positioning of the cannula and prevent leakage of blood from the incision. At this point, the cannula provides a multiplicity of procedural options for the surgeon. For example, when approaching through the ascending aorta, the multi-access cannula enables the simultaneous passage of various fluids, catheters and/or instruments in opposing directions within the lumen of the aortic arch. One possible direction, upstream, provides access to the aortic root, coronary arteries, aortic valve and left ventricle. Through this cannula access, cardioplegia delivery and venting may be achieved. Another possible direction, downstream, provides access to the arch vessels and descending aorta. Through this cannula access, direct perfusion of the arch and corporeal circulation may be achieved or numerous devices may be inserted, such as prioritized perfusion catheters or Intra-Aortic Balloon Pumps. In addition, the present invention may include intra-luminal flow regulators to eliminate the need for cross-clamping of the aorta. Such flow regulators may be positioned between the directional access paths to provide compartmentalization of the aorta. The utilization of any of the aspects of the multi-access cannula are independent. For example, the surgeon may initiate one procedure and decide whether to insert another device at a future time. Thus, the present invention increases operational flexibility, reduces the level of trauma and minimizes the crowding of the surgical field due to its multi-access functionality and distinct sealing capabilities.

BRIEF DESCRIPTION OF THE DRAWINGS

FIG. 9 illustrates a frontal view of a first embodiment of the multi-access cannula in the insertion position;

FIG. 10 illustrates a lateral view of the multi-access cannula of FIG. 9 in the insertion position;

FIG. 11 illustrates the multi-access cannula of FIG. 9 in the active position inserted into the aorta with an occlusion balloon intra-luminal flow regulator segmenting the ascending aorta;

FIG. 12 illustrates a lateral view of a second embodiment of the multi-access cannula with attached pull cords for creating multi-directional flow in the insertion position;

FIG. 13 illustrates a frontal view of the multi-access cannula of FIG. 12 in the insertion position;

FIG. 14 illustrates a frontal view of the multi-access cannula of FIG. 12 in the active position with the pull cords engaged to orient the distal tips of the cannula for multi-directional flow in opposing directions;

FIG. 15 illustrates a frontal view of the multi-access cannula of FIG. 12 in the active position with an optional occlusion balloon intra-luminal flow regulator segmenting the ascending aorta;

DETAILED DESCRIPTION OF THE INVENTION

Figure 1:
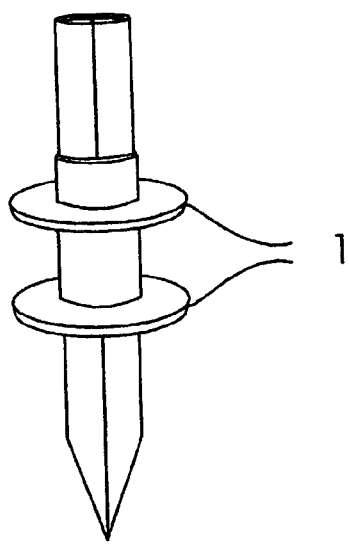
FIG. 1 illustrates an embodiment of the multi-access cannula incorporating a closure seal having two flat sealing disks attached to the main conduit of the multi-access cannula.

The detailed description set forth below in connection with the drawings is intended merely as a description of the presently preferred embodiments of the invention, and is not intended to represent the only form in which the present invention may be constructed or utilized. The description sets forth the designs, functions and methods of implementing the invention in connection with the illustrated embodiments. It is to be understood, however, that the same or equivalent functions and sequences may be accomplished by different embodiments that are also intended to be encompassed within the spirit and scope of the invention.

The preferred embodiments of the present invention are for use in the course of performing conventional open-chest or minimally invasive cardiopulmonary bypass (CPB). In the conventional open-chest procedure, the aorta, typically the ascending aorta, is cannulated with a 20 to 24 French arterial perfusion cannula in the adult patient. In an infant patient, arterial perfusion cannula sizes are approximately 10 to 12 French. Through one such cannula, oxygenated blood is delivered from the CPB pump to the vessels of the aortic arch and the systemic circulation. Proper position of the cannula tip is critical to avoid complications and irreversible injury. Some cannula tips are right-angled to aid in directing flow toward the descending aortic arch. Others are straight, requiring the cannula to be angled so that the tip of the cannula is directed toward the middle of the transverse arch to avoid entering the arch vessels. Once CPB flow is established, the ascending aorta is cross-clamped and cardioplegia is delivered to the coronary arteries to arrest the heart. Cross-clamping may be achieved with the use of traditional external clamping mechanisms or less-invasive internal occlusion methods. If the aortic valve is competent, cardioplegia can be administered through a large-bore needle in the ascending aorta upstream of the clamp. If the aortic valve is incompetent, the ascending aorta can be opened for direct perfusion of the coronary arteries with a specialized catheter. To prevent distension and avoid fibrillation of the heart, a venting catheter may be placed in the left ventricle, either through the ascending aorta and across the aortic valve or through the right superior pulmonary vein.

As described above, the basic aspects of CPB involve numerous procedures which can be damaging to the aorta, particularly cannulation and cross-clamping. In addition, many procedures involve the use of additional devices, such as an intra-aortic balloon pump (IABP), which may crowd the surgical field and further damage the aortic wall. Such damage and crowding may be minimized with the use of the multi-access cannula of the present invention. The multi-access cannula provides multi-directional access to the aortic arch through one insertion site in the aortic wall. One direction, upstream, may be used for access to the aortic root, coronary arteries, aortic valve and left ventricle. Through this cannula access, cardioplegia delivery and venting may be achieved. The opposite direction, downstream, may be used for access to the arch vessels and descending aorta. Through this cannula access, direct perfusion of the body may be achieved or numerous devices may be inserted, such as prioritized perfusion catheters or IABPs. In addition, the present invention may include an intra-luminal flow regulator, such as an occlusion balloon or exterior catheter flow valve, to eliminate the need for cross-clamping of the aorta. Thus, the present invention can dramatically reduce the level of trauma and crowding of the surgical field at the ascending aorta during CPB due to its multi-access functionality.

The multi-access cannula of the present invention may be provided in a number of embodiments that achieve the described functionality, namely to provide multi-directional access to the aortic arch through one insertion site in the aortic wall. Though each of the embodiments will involve a unique design and mechanism to achieve this goal, a few aspects are common to all.

First, each embodiment will enter the aorta through one incision, which may be but is not limited to the range of 20–24 French. Standard cannulation procedures may be used. This may involve placing two concentric purse-string sutures in the aortic adventitia and media at the proposed site of cannulation. The aorta may then be incised as by a stab wound within the purse-string suture, and the cannula may be directly inserted. The inner purse-string suture may then be secured as a tourniquet and tied to the cannula. As the cannula is removed after CPB, the outer purse-string suture is crossed while the inner purse-string is tied. The outer purse-string suture is then tied and hemostasis is established.

It is apparent that such a procedure can be injurious to the aortic wall and may lead to surgical complications. For example, puncture of a vessel wall may lead to the introduction of infection, air bubble entrapment, or major post-operative bleeding. Other catastrophic complications related to direct insertion of cannulas include: a) the risk of splitting the three layers of the aortic wall apart (known as aortic dissection), and b) the risk of disruption of cholesterol and/or calcium deposits from the innermost layer of the aortic wall at the site of entry, which can then be carried into the blood stream to occlude flow in distal arterial branches and reduce function in vital organs such as the brain (stroke), kidneys (renal failure), legs (gangrene), bowel (gangrene), liver (hepatic failure). Therefore, each of the embodiments will involve only one puncture of the aortic wall. In addition, a specially designed closure seal may be utilized at the point of entry to reduce trauma to the aortic wall and reduce the risk of leakage, air bubble introduction and bleeding from multiple sutures.

The closure seal may comprise a variety of designs, and it may be integral with, mounted upon, completely independent of, or a combination of these and other possibilities, in relation to the multi-access cannula. Particularly when it is embodied as a separate device, the closure seal will preferably also include a hemostasis valve or similar seal for sealing a central passage through the closure seal when a cannula or other instrument is inserted or withdrawn through the central passage. In general, the closure seal will be positioned at the point of entry of the cannula with the vessel wall. The sealing mechanism will thus strategically straddle the vessel wall at the puncture site. The proximal side of the closure seal will bear against the outside of the vessel wall, which not only prevents further advancement into the vessel, like a traditional locator ring, but also acts as a partial seal to prevent leakage of blood from the puncture site. The distal side of the closure seal will lie intraluminally and will bear against the inside surface of the vessel forming a clamping mechanism with the proximal side. Thus, the closure seal will provide a clamping arrangement that will reduce injury to the aortic wall and reduce the risk of leakage at the puncture site. Upon removal of the cannula, the puncture site may be closed with a variety of methods, depending on the closure seal design. The closure seal may be removed and the puncture site closed with traditional methods, such as tying off a purse-string suture, or alternative methods. Or, the closure seal may remain in place to serve as a plug to the puncture site. The plug may be biologically inert and remain as a permanent implant, or may be partly or wholly biological or biodegradable to permanently grow into or become part of the vessel wall.

Figure 2:
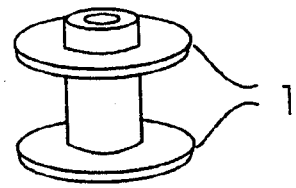
FIG. 2 illustrates an embodiment of a closure seal having two flat sealing disks, but which is separate from the main conduit of the multi-access cannula.

A few embodiments of the closure seal are described as follows. A first embodiment, shown in FIGS. 1 & 2, involves two flat disks 1 similar to catheter retention discs. These may be formed from a variety of metals, polymers or biomaterials and thus may vary in compliance from rigid to flexible. The inner and outer disks 1 may be mounted on the distal end of the multi-access cannula (FIG. 1), they may form an independent device similar in shape to a sewing bobbin (FIG. 2), or independent and mounted parts may operate in conjunction upon proper placement of the cannula. When constructed as a separate sealing device, as in FIG. 2, the closure seal preferably also includes a hemostasis valve or similar seal for sealing a central passage through the closure seal when a cannula or other instrument is inserted or withdrawn through the central passage. The disks 1, and in particular the distal or inner disk, may have a low profile for easy insertion across the vessel wall and then open into the disk shaped design when in position, or the disks 1 may be positioned across the vessel wall in the full open arrangement. Compression of the disks 1 to form the clamping action may be achieved and secured with any manner of pull ties, sutures, staples or other mechanism. Upon removal of the cannula, the closure seal may be removed or left behind as an implant. In the latter case, the opening through which the cannula has passed may be occluded with a variety of methods, including plugs, bindings, or grafts.

Figure 3:
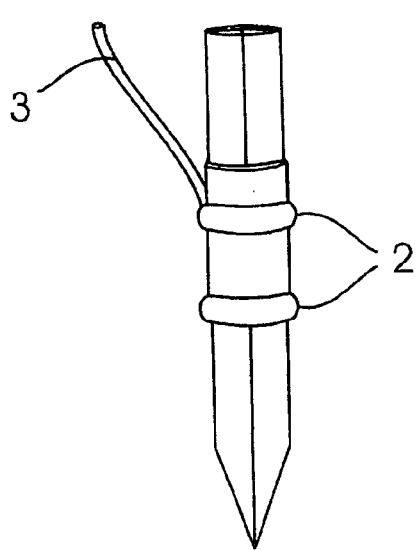
FIG. 3 illustrates an embodiment of the multi-access cannula incorporating a closure seal having two inflatable sealing disks attached to the main conduit of the multi-access cannula depicted in the deflated state.
Figure 4:
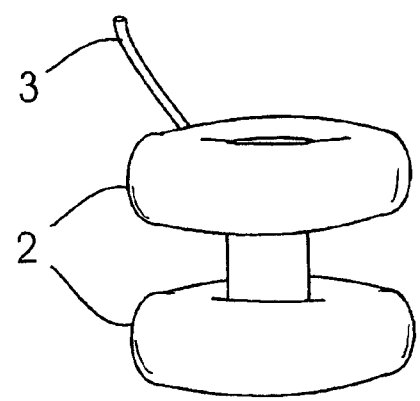
FIG. 4 illustrates an embodiment of a closure seal separate from the main conduit of the multi-access cannula having two inflatable sealing disks depicted in the inflated state.

Another embodiment of the closure seal, shown in FIGS. 3 & 4, may incorporate inner and outer inflatable disks 2. These may be formed from a variety of polymer materials and may be inflated by pumping or injecting a gas or liquid into a port 3 leading to the inflatable disks 2, individually or in combination. Again, these disks may be mounted on the distal end of the multi-access cannula (FIG. 3), they may form an independent device similar in shape to a sewing bobbin (FIG. 4), or independent and mounted parts may operate in conjunction upon proper placement of the cannula. When constructed as a separate sealing device, as in FIG. 4, the closure seal preferably also includes a hemostasis valve or similar seal for sealing a central passage through the closure seal when a cannula or other instrument is inserted or withdrawn through the central passage. Due to their inflatable nature, they may have a low profile for easy insertion across the vessel wall. Inflation will activate the disks and compress the disks together to form the clamping action. Upon removal of the cannula, the closure seal may be removed after deflation or left behind as an implant. In the latter case, the opening through which the cannula had passed may be occluded by any of the methods mentioned above or by further inflation of the disks 2.

Figure 5:
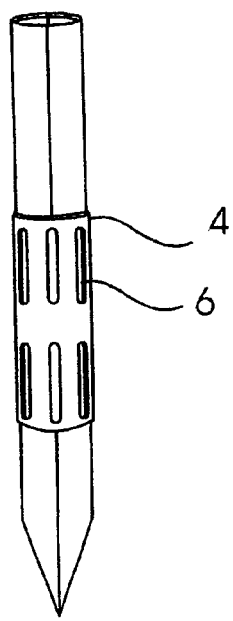
FIG. 5 illustrates an embodiment of the multi-access cannula incorporating a closure seal having an expandable catheter sleeve depicted in an undeployed state.
Figure 6:
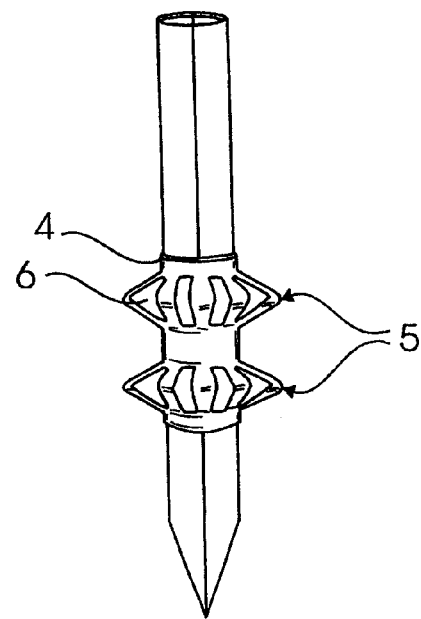
FIG. 6 illustrates the multi-access cannula of FIG. 5 with the expandable catheter sleeve of the closure seal in a deployed state.

As shown in FIGS. 5 & 6, the closure seal may also incorporate expandable members, such as slotted catheter sleeves 4, that expand or "mushroom" outward when axially compressed to form inner and outer disk shaped appendices 5. These may be formed from a variety of polymers or similar functioning materials. The sleeve 4 may be mounted on the distal end of the multi-access cannula (FIG. 5), it may form an independent device, or independent and mounted parts may operate in conjunction upon proper placement of the cannula. Like the inflatable disks 2, the expandable sleeves 4 may have a low profile for easy insertion across the vessel wall. The expanding action may be activated (FIG. 6) with a variety of methods, such as pulling an attachment connected to the base of the sleeve 4 or pushing the sleeve 4 in relation to an attachment at the base. A flexible sheath may also encase the sleeve 4 to prevent any leakage through the slits 6 of the mushroomed area. Upon removal of the cannula, the closure seal may be removed by reversing the expanding action or left behind as an implant. In the latter case, the opening through which the cannula has passed may be occluded by any of the methods mentioned above.

Figure 7:
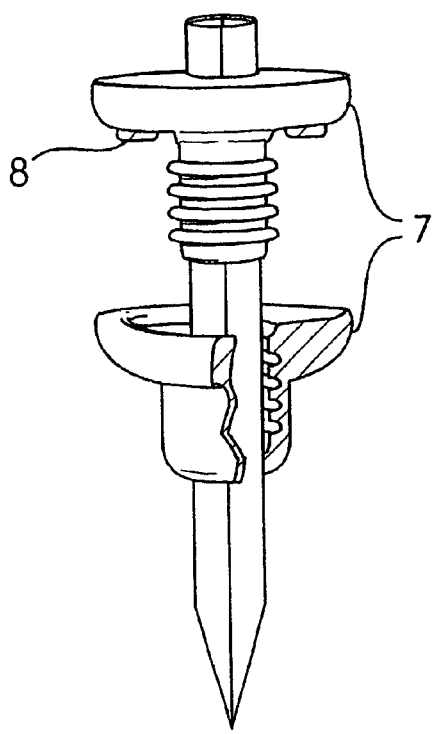
FIG. 7 illustrates an embodiment of the multi-access cannula incorporating a closure seal in the form of disk-type sections that screw together.
Figure 8:
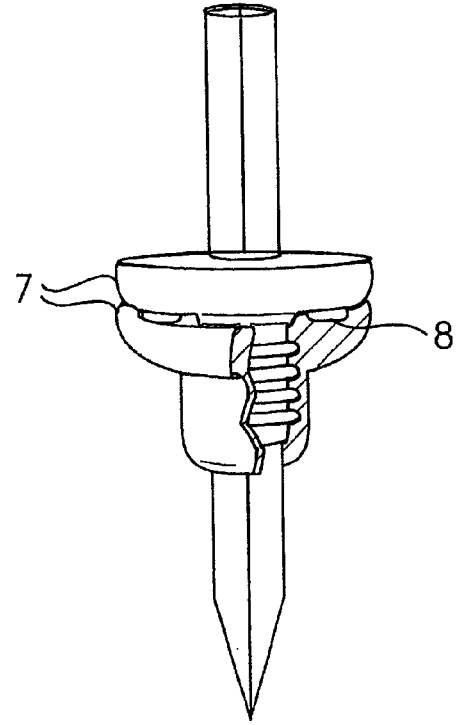
FIG. 8 illustrates the multi-access cannula of FIG. 7 with the closure seal screwed together in the clamped position.

The closure seal designs may also incorporate inner and outer disk-type sections 7 that screw together with a hollow threaded stem, as shown in FIGS. 7 & 8. These may be formed from a variety of metals, polymers or biomaterials and thus may vary in compliance from rigid to flexible. The disk-type sections 7 may be mounted on the distal end of the multi-access cannula (FIG. 7), they may form an independent device, or independent and mounted parts may operate in conjunction upon proper placement of the cannula. Preferably, a hemostasis valve or similar seal seals the central passage through the hollow threaded stem when a cannula or other instrument is inserted or withdrawn through the central passage. Compression of the disks to form the clamping action may be achieved and secured by screwing the top portion into the base (FIG. 8). Gaskets 8 may be incorporated to supplement the sealing capability. Again, upon removal of the cannula, the closure seal may be removed or left behind as an implant. In the latter case, the opening through which the cannula has passed may be occluded with a variety of methods mentioned above. Any of these closure seal embodiments may be adapted to include additional attributes or functionality, or they may be hybrid designs of those described.

Second, each embodiment of the multi-access cannula may optionally include an integrated intra-luminal flow regulator, such as an occlusion balloon or an exterior catheter flow control valve. Exterior catheter flow control valves suitable for this application can be found in commonly owned, copending U.S. patent applications Ser. Nos. 08/665,635, 08/664,361 and 08/664,360, filed Jun. 17, 1996, the specifications of which are hereby incorporated by reference in their entirety. It has been demonstrated that an intra-luminal flow regulator can successfully occlude the aorta during CPB as an alternative to the conventional cross-clamp. It was found that the use of an intra-luminal flow regulator in this manner has many advantages over the use of a cross-clamp. To begin with, in cases of very severe calcification of the ascending aorta, it is not feasible to apply an external clamp because the compressibility of the aorta has been lost. Surgeons must then resort to less optimal, more complex methods of CPB support, myocardial protection and heart isolation which further increases the likelihood of post-operative complications. In cases of moderate calcification, the compressing or squeezing action of the clamp can dislodge fragments of cholesterol or calcium from the aortic wall. These fragments can embolize downstream in vital organs causing irreversible damage and injury. The intra-luminal flow regulator expands within the lumen of the aorta until it sufficiently or completely blocks the flow of blood. This minimizes the dislodgment of calcified fragments and allows the occlusion of incompressible aortas.

The collapsed intra-luminal flow regulator may be mounted on the multi-access cannula in a position that will enable proper inflation when the cannula is inserted. Such a flow regulator may be comprised of a variety of polymeric materials, such a vinyl, various polyolefins, polyurethanes, silicones, PET, nylon, and latex, and it may be capable of expanding from an unexpanded to an expanded state by inflation. If inflatable, the flow regulator may be expanded by pumping or injecting a gas or liquid into a port leading to the inflatable member. Upon inflation, the member will surround at least part of the intra-luminal portion of the cannula and will expand around any obstacles to fill the lumen of the aorta and block residual blood flow. The flow regulator will not block or interfere with the placement of or access through any direction of the multi-access cannula. In fact, the flow regulator will typically reside between access directions, allowing communication with independent sections of the aorta. Therefore, for example, when the flow regulator is activated or inflated, antegrade cardioplegia may be delivered through one access direction to the isolated segment of the ascending aorta just below the flow regulator into the coronary ostia. Likewise, systemic arterial perfusion flow, prioritized perfusion flow or various devices may simultaneously access the aorta in the opposite direction, downstream of the flow regulator. Thus, the intra-luminal flow regulator may be used in place of the cross-clamp in standard open-chest or minimally invasive CPB procedures, avoiding the associated complications and aiding in the multi-purpose functionality of the present invention.

A first embodiment of the multi-access cannula of the present invention is depicted in FIGS. 9–11. In this embodiment, the multi-access cannula 9 may be comprised of but does not necessarily include nor is limited to the following: a first access leg 10, a second access leg 11, hemostatic valves within the access legs, a closure seal 12 and an intra-luminal flow regulator 13. The first access leg 10 is a first lumen defined by a first lumen wall. The sizes and cross-sectional shapes of the first lumen may vary, but generally are selected to provide optimum blood flow range during CPB or optimum compatibility with insertable catheters or a combination of these functions. If catheters are to be used, the lumen may contain a hemostatic valve. Known hemostatic valves generally include passive self-closing valves, "open hole" valves and "active" valves. The hemostatic valves which may be used in the present invention may be of a single valve type or a combination of valve types selected from the above mentioned types or other types of valves according to the desired application.

The second access leg 11 is a second lumen defined by a second lumen wall. The sizes and cross-sectional shapes of the second lumen may vary, but generally are selected to provide optimum flow range for cardioplegia during CPB or optimum compatibility with insertable catheters or a combination of these functions. Again, if catheters are to be used, the lumen may contain a hemostatic valve. Likewise, the hemostatic valves which may be used in the present invention may be of a single valve type or a combination of valve types selected from the above mentioned types or other types of valves according to the desired application.

FIGS. 9 and 10 depict the first embodiment of the multi-access cannula 9 in position 1, the insertion position. Here the first access leg 10 and the second access leg 11 of the cannula 9 are parallel to one another, providing a profile resembling the letter "I" or a single lumen cannula. The access legs 10, 11 are maintained in position 1 by any locking means, such as interlocking cross-sectional lumen shapes, interlocking grooves between the legs, or any type of binding mechanism or material integral or used in conjunction with the present invention. In the insertion position, the multi-access cannula 9 is inserted through the wall 14 of the aorta 15 to an appropriate depth. At this depth, the closure seal 12 may be engaged to secure the cannula 9 and prevent leakage of blood from the incision. FIG. 9 portrays a side view of the cannula 9, through a cross-section of the aorta 15 facing downstream. This view reveals that the cannula 9 is comprised of two separate lumens. FIG. 10 portrays a 90 degree shift to a frontal view, as if to view the cannula 9 through the anterior wall of the aorta 15. This allows the identification of the first access leg 10 with the lumen opening 16 at the tip.

FIG. 11 depicts the first embodiment of the multi-access cannula 9 in position 2, the active position. Here the first access leg 10 and the second access leg 11 of the cannula 9 are perpendicular to one another, providing a profile resembling the letter "X". The access legs 10, 11 may be manually transposed or pivoted from position 1 to position 2, and back to position 1 for removal. The access legs 10, 11 are maintained in position 2 by any locking means, such as interlocking cross-sectional lumen shapes, interlocking grooves between the legs, or any type of binding mechanism or material integral or used in conjunction with the present invention. At this point, the optional intra-luminal flow regulator 13 may be expanded by any means, such as pumping or injecting a gas or liquid into a port leading to the flow regulator structure. Upon inflation, the flow regulator 13 will typically reside between the two access legs 10, 11, expanding around the legs 10, 11 to fill the lumen of the aorta 15. Such positioning will divide the aorta 15 into two independent cavities 17, 18. The first cavity 17 receives the distal end of the first access leg 10, which provides an access path or channel through which communication may be made with the first cavity 17. For example, the outlet of the CPB pump may communicate with the systemic circulation via the first access leg 10. Alternatively or additionally, flexible catheters, cannulas or devices may be inserted through the first access leg 10 for use in the first cavity 17. The second cavity 18 receives the distal end of the second access leg 11, which provides an access path or channel through which communication may be made with the second cavity 18. For example, the outlet of the cardioplegia pump may communicate with the aortic root and coronary arteries via the second access leg 11. Alternatively or additionally, flexible catheters, cannulas or devices, such as a pigtail venting catheter, may be inserted through the second leg 11 for use in the left ventricle. Such a design allows for numerous procedures in both upstream and downstream independent and isolated directions with only one incision site.

A second embodiment of the multi-access cannula 19 of the present invention is depicted in FIGS. 12–15. In this embodiment, the multi-access cannula 19 may be comprised of but does not necessarily include nor is limited to the following: a first access leg 20, a second access leg 21, hemostatic valves within the access legs, a first pull-cord 22, a second pull-cord 23, a closure seal 12 and an intra-aortic flow regulator 13. The first access leg 20 is a first lumen defined by a first lumen wall. The sizes and cross-sectional shapes of the first lumen may vary, but generally are selected to provide optimum blood flow range during CPB or optimum compatibility with insertable catheters or a combination of these functions. If catheters are to be used, the lumen may contain a hemostatic valve. Known hemostatic valves generally include passive self-closing valves, "open hole" valves and "active" valves. The hemostatic valves which may be used in the present invention may be of a single valve type or a combination of valve types selected from the above mentioned types or other types of valves according to the desired application.

The second access leg 21 is a second lumen defined by a second lumen wall. The sizes and cross-sectional shapes of the second lumen may vary, but generally are selected to provide optimum flow range for cardioplegia during CPB or optimum compatibility with insertable catheters or a combination of these functions. Again, if catheters are to be used, the lumen may contain a hemostatic valve. Likewise, the hemostatic valves which may be used in the present invention may be of a single valve type or a combination of valve types selected from the above mentioned types or other types of valves according to the desired application.

FIGS. 12 and 13 depict the second embodiment of the multi-access cannula 19 in position 1, the insertion position. Here the first access leg 20 and the second access leg 21 of the cannula are parallel to one another, providing a profile resembling the letter "I" or a single lumen cannula. The access legs are maintained in position 1 by any locking means, such as interlocking cross-sectional lumen shapes, interlocking grooves between the legs, or any type of binding mechanism or material integral or used in conjunction with the present invention. In the insertion position, the multi-access cannula 19 is inserted through the wall of the aorta to an appropriate depth. At this depth, the closure seal 12 may be engaged to secure the cannula and prevent leakage of blood from the incision. FIG. 12 portrays a side view of the cannula 19, through a cross-section of the aorta 15 facing downstream. This view allows identification of the second access leg 21. FIG. 13 portrays a 90 degree shift to a frontal view, as if to view the cannula 19 through the anterior wall of the aorta 15. This reveals that the cannula 19 is comprised of two separate lumens.

FIGS. 14 and 15 depict the second embodiment of the multi-access cannula 19 in position 2, the active position. As shown in FIG. 14, the access legs 20, 21 may be manually translated or articulated from position 1 to position 2 by pulling the first and second pull-cords 22, 23. The first pull-cord 22 may be integrally or superficially bonded, interdigitated or attached by any number of methods along the length of the first access leg 20 or it may reside it a separate lumen along the length of the first access leg 20. Pulling the pull-cord will cause the length of the attached access leg to contract and curl toward the attached cord. For example, pulling the first pull-cord 22 will cause the lower portion of the first access leg 20 to curl upward and the distal tip of the first access leg 20 to raise within the lumen of the aorta 15. The degree of curvature is directly correlated to the extent of the pull motion. The second pull-cord 23 may be similarly attached to the second access leg 21 or it may reside in a separate lumen along the length of the second access leg 21, and it functions in the same manner as that in the first access leg 20. Therefore, the first and second access legs 20, 21 may be independently positioned within the lumen of the aorta 15 to provide customized bi-directional access to the aorta 15. When the legs are so positioned, the profile resembles an upside-down letter "Y".

The access legs 20, 21 are maintained in position 2 by any locking means, any type of binding mechanism or material integral or used in conjunction with the present invention. When locked, the pull-cords 22, 23 will be secured, providing the required tension to hold the legs 20, 21 at the proper angle. At this point, as seen in FIG. 15, the optional intra-luminal flow regulator 13 may be expanded by pumping or injecting a gas or liquid into a port leading to the flow regulator structure. Upon inflation, the flow regulator 13 will typically reside between the two access legs 20, 21, expanding around the legs 20, 21 to fill the lumen of the aorta 15. Such positioning will divide the aorta 15 into two independent cavities 24, 25. The cavities 24, 25 will receive the access legs 20, 21 in a manner similar to that in the first embodiment, and therefore will not be further described. The access legs 20, 21 may be returned to position 1 by releasing the locking mechanism. The pullcords 22, 23 will then relaxed and the profile of the multi-access cannula 19 will return to the first position resembling the letter "I". The cannula 19 may then be removed.

A third embodiment of the multi-access cannula 26 of the present invention is depicted in FIGS. 16–22. In this embodiment, the multi-access cannula 26 may be comprised of but does not necessarily include nor is limited to the following: a primary access conduit 27, a primary access side port 28, a secondary access conduit 29, hemostatic valves within the access legs and/or side port, a closure seal 12 and an intra-luminal flow regulator 13. The primary access conduit 27 is a tubular structure with of a perfusion or primary lumen defined by a primary lumen wall. In general, the primary access conduit 27 will resemble the size and dimensions of traditional right-angle tipped arterial perfusion cannulas and will be utilized to provide the same function. Thus, the sizes and cross-sectional shapes of the primary lumen may vary, but generally are selected to provide optimum blood flow range during CPB.

The primary access side port 28 is a side lumen of short length defined by a side lumen wall. The side port 28 is located above the heel of the right-angle tipped primary access conduit 27 and will be accessible from outside of the aoirta 15 when the cannula 26 is in place. Flexible catheters, cannulas and other devices may be inserted through the primary access side port 28 to the lumen of the primary access conduit 27 and out of its distal end 30. Thus, devices may access the aorta 15 in the same direction as CPB blood flow through an arterial perfusion type cannula with the use of the primary access side port 28. To aid in such maneuvers, the primary access side port 28 may be angled downward toward the tip of the primary access cannula 27. In addition, a hemostatic valve may be positioned between the side port 28 and the primary lumen 27. The hemostatic valve may be a single valve type or a combination of valve types selected according to the desired application. The sizes, cross-sectional shapes and types of hemostatic valves may vary but generally are selected to provide optimum compatibility with insertable catheters.

The secondary access conduit 29 is a secondary lumen defined by a secondary lumen wall. The sizes and cross-sectional shapes of the second lumen may vary, but generally are selected to provide optimum flow range for cardioplegia during CPB or optimum compatibility with insertable catheters or a combination of these functions. Again, if catheters are to be used, the lumen may contain a hemostatic valve. Likewise, the hemostatic valves which may be used in the present invention may be of a single valve type or a combination of valve types selected from the above mentioned types or other types of valves according to the desired application.

The design, location and path of the secondary access conduit 29 may also vary, but in general, the inlet 31 of the secondary access conduit 29 lies upstream of the outlet 32 of the secondary access conduit 29 along the length of the primary access conduit 27. Preferably, the inlet 31 and outlet 32 of the secondary access conduit 29 lie on the same side of the primary access conduit 27, as shown, so that the secondary access conduit 29 does not cross over the primary access conduit 27. Alternatively, the inlet 31 and outlet 32 of the secondary access conduit 29 may lie on opposite sides of the primary access conduit 27 so that the secondary access conduit 29 will cross over the primary access conduit 27. In addition, when the cannula 26 is inserted, the inlet 31 will lie outside of the aorta 15 and the outlet 32 will lie intraluminally, in a direction opposing that of the distal tip of the primary access conduit 27.

Figure 18:
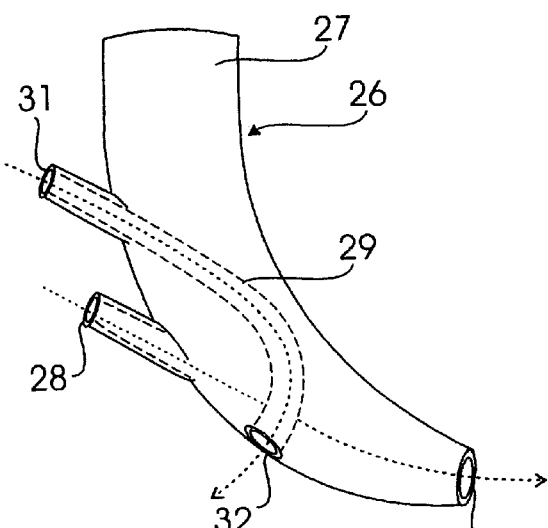
FIG. 18 illustrates a first variation of the multi-access cannula of FIG. 16 where the secondary access side conduit is in communication with the primary access conduit.
Figure 19:
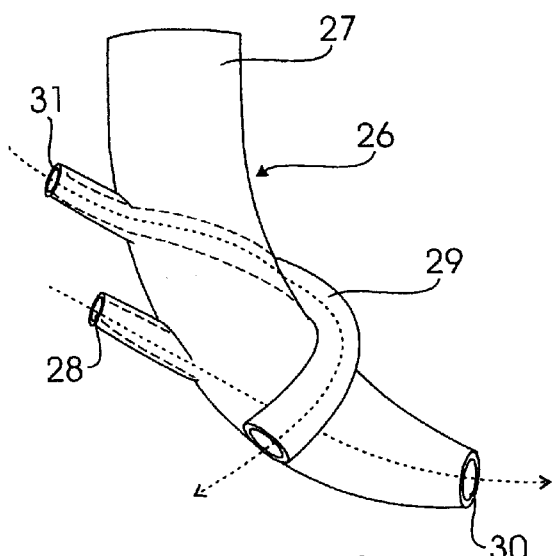
FIG. 19 illustrates a second variation of the multi-access cannula of FIG. 16 where the secondary access side conduit wraps around the primary access conduit and there is no communication.
Figure 20:
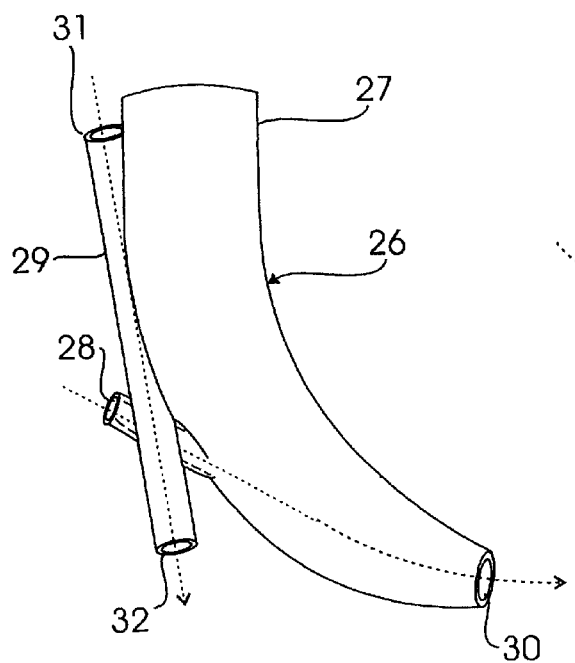
FIG. 20 illustrates a third variation of the multi-access cannula of FIG. 16 where the secondary access side conduit extends along the length of the primary access conduit and there is no communication.

FIGS. 18–21 depict possible alternative designs, locations and paths for the secondary access conduits 29. As seen in FIG. 18, the secondary access conduit 29 may form a U-turn along the anterior or posterior portion of the primary access conduit 27. Likewise, as seen in FIG. 19, the secondary access conduit 29 may wrap around the primary access conduit 27, from the posterior to the anterior side of the primary access conduit 27. In FIG. 20, the secondary access conduit 29 may form a relatively linear path along the length of the primary access conduit 27. Here the inlet 31 to the secondary access catheter 29 will lie upstream of the outlet 32, which will reside near the heel of the right-angle tipped primary access cannula 27. In each of these cases, the secondary access conduit 29 will be formed and attached externally, internally or in combination in relation to the primary access conduit 27, and there will be no communication between the primary 27 and secondary 29 access conduits. Therefore, the flow path through the secondary access conduit 29 may be used for, among other uses, the passage of cardioplegia, the evacuation of fluid from the aortic root and left ventricle, and the insertion of various catheters to perform these tasks.

Figure 21:
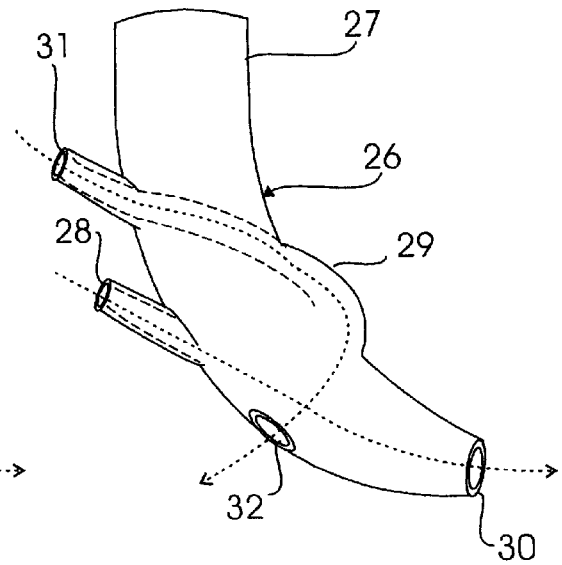
FIG. 21 illustrates a fourth variation of the multi-access cannula of FIG. 16 where the secondary access side conduit is in communication with the primary access conduit.

As seen in FIG. 21, the secondary access conduit 29 may form a U-turn within the primary access conduit 27. In this case, the primary 27 and secondary 29 access conduits will be in direct communication, hence a flexible catheter must be used to delivery cardioplegia or evacuate fluid through the secondary access conduit 29. The flexible catheter may enter at the inlet port 31 of the secondary access conduit 29, traverse the width of the primary access conduit 27, deflect off of the opposing side of the primary access lumen 27 in a U-turn fashion, and return across the width of the primary access conduit 27 to the outlet port 32 of the secondary access conduit 29. Grooves, curvatures, insets or other mechanisms in the primary access conduit 27 may assist in this maneuver.

Figure 16:
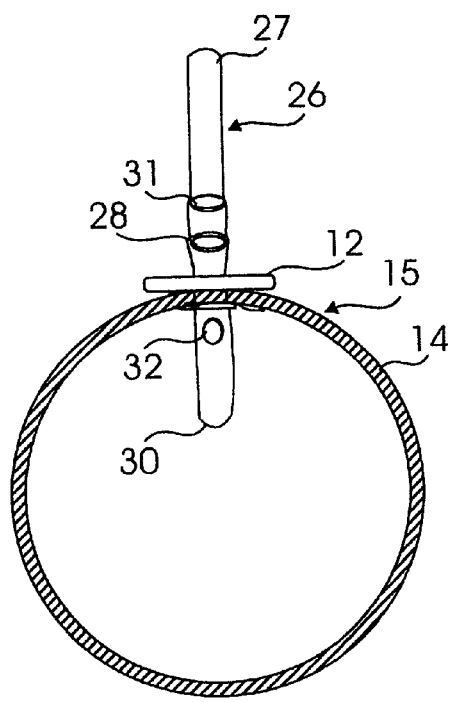
FIG. 16 illustrates a lateral view of a third embodiment of the multi-access cannula inserted into a patient's ascending aorta.
Figure 17:
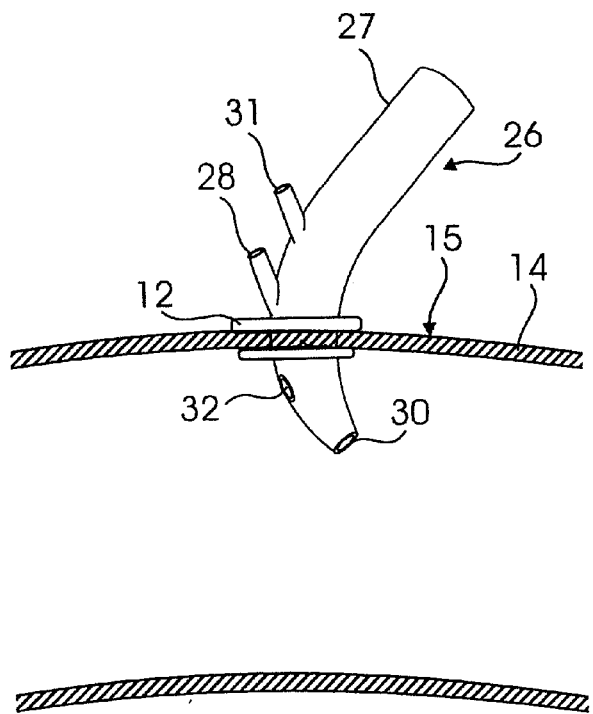
FIG. 17 illustrates a frontal view of the multi-access cannula of FIG. 16.
Figure 22:
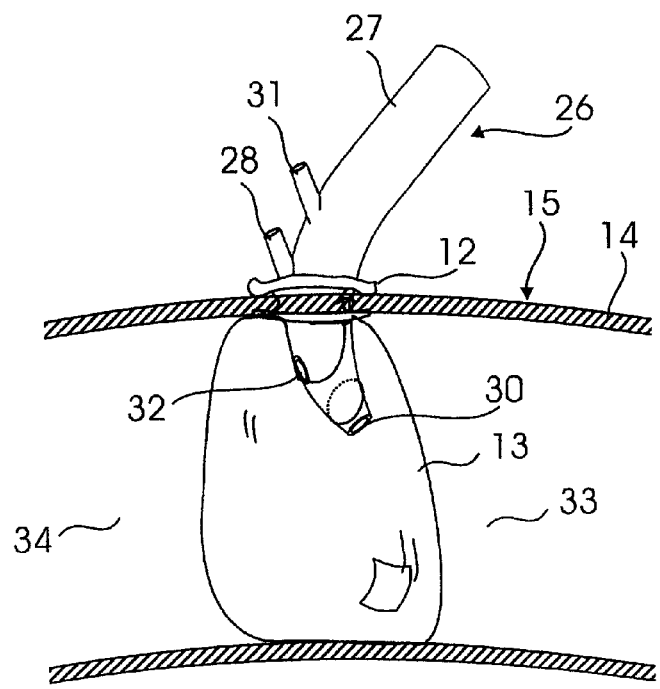
FIG. 22 illustrates a frontal view of the multi-access cannula of FIG. 16 in the active position with an optional occlusion balloon intra-luminal flow regulator segmenting the ascending aorta.

FIGS. 16, 17 and 22 depict the third embodiment of the multi-access cannula 26 upon insertion into the aorta 15. Here the cannula 26 maintains the same position when inserted and in use. The cannula is inserted through the wall 14 of the aorta 15 to an appropriate depth. At this depth, the closure seal 12 is appropriately positioned and may then be engaged to secure the cannula 26 and prevent leakage of blood from the incision. FIG. 16 portrays a side view of the cannula 26, through a cross-section of the aorta 15 facing downstream. This view depicts the length of the cannula 26 opposite the opening of the primary access conduit tip, i.e. the straight portion of the cannula leading to the heel as the cannula bends at a right angle downstream. The inlet 31 and outlet 32 of the secondary access conduit 29 and the inlet of the primary access side port 28 are visible. FIG. 17 portrays a 90 degree shift to a frontal view of the third embodiment of the present invention within the patient's aorta.

FIG. 22 depicts the third embodiment of the multi-access cannula 26 with the optional intraluminal flow regulator 13 in place. The flow regulator 13, in this case an occlusion balloon, may be expanded by pumping or injecting a gas or liquid into a port leading to the flow regulator structure. Upon inflation, the balloon 13 will typically reside between the outlets of the primary 27 and secondary access conduits 29, expanding around the tip of the primary access conduit 27 to fill the lumen of the aorta. Alternatively, the intraluminal flow regulator 13 may be in the form of an external catheter flow valve located between the outlets of the primary 27 and secondary access conduits 29. Such positioning will divide the aorta into two independent cavities 33, 34. The cavities will receive the outlets to the access conduits in a manner similar to that in the first and second embodiments, and therefore will not be further described.

In each of the embodiments of the multi-access cannula of the present invention, the cannula body will be composed of a biologically compatible material. Such a material may be rigid or elastomeric in nature. As is apparent from the second embodiment of the multi-access cannula 19, a flexible or elastomeric material may be preferable or required for portions of the access legs 20, 21 of the multi-access cannula 19. Here the bending action of the access legs 20, 21 upon tensing of the pull-cords 22, 23, requires a flexible or elastomeric material in this region. However, each and any embodiment may be constructed of rigid, flexible, elastomeric materials or a combination of materials for any of its parts.

Flexible or elastomeric embodiments are most advantageously made of a clear or translucent elastomeric material, such as silicone rubber. Such translucence facilitates safe use by allowing visual monitoring of blood flow through the cannula. Thus, formation of any gas bubbles or blood clots may be detected during a procedure such as CPB. The elastomeric structure also facilitates safe and efficient sealing of various connectors to the body of the cannula. Tube connectors may be provided at the ends of the access legs or conduits with radial barbed fittings to form a secure seal between the tubing and the body of the cannula.

Rigid embodiments may be constructed of light-weight, solid-plastic material, preferably rigid PVC, polycarbonate or acrylic. It is known that manufacture of molded rigid plastic or metal components can be automated and regulated to provide exact tolerances. Moreover, a rigid body can be adapted for a variety of applications by selecting from among various internal component parts having different characteristics, such as material composition, lumen size, valve type and valve opening size. Thus, an embodiment comprising a rigid body and selected internal components can provide closely controlled, tightly toleranced passages and efficient sealing about catheters, cannulas and other devices inserted through such components.

Although the invention has been described herein with specific reference to presently preferred embodiments thereof, it will be appreciated by those skilled in the art that various additions, modifications, deletions and alterations may be made to such preferred and exemplary embodiments without departing from the spirit and scope of the invention.

What is claimed is:

1. A multi-access perfusion cannula comprising:
   (a) an elongated tubular cannula body including a plurality of pivoting access legs;
   (b) a downstream directed perfusion lumen within said elongated tubular cannula body;
   (c) an upstream directed access conduit within said elongated tubular cannula body configured for passage of a catheter or instrument; and
   (d) an intra-luminal flow control regulator, said intra-luminal flow control regulator capable of at least partially occluding a vessel.

2. The multi-access perfusion cannula of claim 1, wherein said perfusion lumen comprises a proximal port and a distal perfusion port, said proximal port in being communication with said perfusion lumen and said distal perfusion port being in communication with said perfusion lumen, said perfusion lumen being of sufficient cross-sectional size and shape to provide for compatibility with insertable catheters and perfusion blood flow for cardiopulmonary support.

3. The multi-access perfusion cannula of claim 1, wherein said said plurality of pivoting access legs comprise a first pivoting access leg and a second pivoting access leg, said perfusion lumen extending through said first pivoting access leg, said perfusion lumen being of sufficient size and shape to provide perfusion to blood flow for cardiopulmonary support and compatibility with insertable catheters, said access conduit extending through said second pivoting access leg, said access conduit being capable of directing a second insertable catheter in an upstream direction opposing that of said first pivoting access leg, said access conduit being of sufficient cross sectional size and shape to provide for compatibility with insertable catheters and flow of cardioplegic agent.

4. The multi-access perfusion cannula of claim 1 further comprising a locking mechanism for selectively locking said pivoting access legs in an active position wherein said pivoting access legs supply multi-direction flow in a downstream direction and an upstream direction simultaneously and independently.

5. The multi-access perfusion cannula of claim 1 further comprising at least one hemostasis valve having a passage therethrough and capable of maintaining a fluidly tight seal upon introduction of an extendable member.

6. The multi-access perfusion cannula of claim 1, further comprising an insertion tip capable of percutaneous entrance into a vessel.

7. A multi-access perfusion cannula comprising:
   (a) an elongated tubular cannula body including a plurality of articulating access legs;
   (b) a downstream directed perfusion lumen within said elongated tubular cannula body;
   (c) an upstream directed access conduit within said elongated tubular cannula body configured for passage of a catheter or instrument; and
   (d) a sealing mechanism having a proximal portion and a distal portion, said proximal portion covering an insertion site on an outside surface of a vessel wall by securing a distal surface of said proximal portion of said sealing mechanism against the outside surface of the vessel, said distal portion of said sealing mechanism lying intraluminally of the vessel wall with a proximal surface of said distal portion of said sealing mechanism bearing against the inside surface of the vessel.

8. The multi-access perfusion cannula of claim 7, wherein said perfusion lumen comprises a proximal port and a distal perfusion port, said proximal port being in communication with said perfusion lumen and said distal perfusion port being in communication with said perfusion lumen, said perfusion lumen being of sufficient cross-sectional size and shape to provide for compatibility with insertable catheters and perfusion blood flow for cardiopulmonary support.

9. The multi-access perfusion cannula of claim 7, wherein said said plurality of articulating access legs comprise a first articulating access leg and a second articulating access leg, said perfusion lumen extending through said first articulating access leg, said perfusion lumen being of sufficient size and shape to provide perfusion to blood flow for cardiopulmonary support and compatibility with insertable catheters, said access conduit extending through said second articulating access leg, said access conduit being capable of directing a second insertable catheter in an upstream direction opposing that of said first articulating access leg, said access conduit being of sufficient cross sectional size and shape to provide for compatibility with insertable catheters and flow of cardioplegic agent.

10. The multi-access perfusion cannula of claim 9 further comprising an articulating mechanism including a first articulating cord and a second articulating cord, said first articulating cord having a proximal end and a distal end, said distal end fixedly attached to said first articulating access leg, engagement of said first articulating cord causing articulation of first articulating access leg, said second articulating cord having a proximal end and a distal end, said distal end fixedly attached to said second articulating access leg, engagement of said second articulating cord causing articulation of second articulating access leg, said first articulating access leg and said second articulating access leg being deployable simultaneously or independently and in differing degrees of articulation.

11. The multi-access perfusion cannula of claim 7 further comprising a locking mechanism for selectively locking said articulating access legs in an active position wherein said articulating access legs supply multi-direction flow in a downstream direction and an upstream direction.

12. The multi-access perfusion cannula of claim 7 further comprising an intra-luminal flow control regulator, said intra-luminal flow control regulator capable of at least partially occluding a vessel.

13. The multi-access perfusion cannula of claim 7, further comprising at least one hemostasis valve, said hemostasis valve having a passage therethrough and capable of maintaining a fluidly tight seal upon introduction of an extendable member.

14. The multi-access perfusion cannula of claim 7, further comprising an insertion tip capable of percutaneous entrance into a vessel.

15. A multi-access perfusion cannula comprising:

(a) an elongated tubular cannula body including a plurality of pivoting access legs;

(b) a downstream directed perfusion lumen within said elongated tubular cannula body;

(c) an upstream directed access conduit within said elongated tubular cannula body configured for passage of a catheter or instrument; and (d) a sealing mechanism for sealing an insertion site of said cannula body into a vessel, having a proximal portion and a distal portion, said proximal portion covering the insertion site on an outside surface of a vessel wall by securing a distal surface of said proximal portion of said sealing mechanism against the outside surface of the vessel, said distal portion of said sealing mechanism lying intraluminally of the vessel and covering the insertion site on an inside surface of the vessel wall with a proximal surface of said distal portion of said sealing mechanism bearing against the inside surface of the vessel.

16. The multi-access perfusion cannula of claim 15 further comprising a compression mechanism for urging said proximal portion and said distal portion into engagement with the wall of the vessel.

17. The multi-access perfusion cannula of claim 16, wherein said portion comprises a proximal sealing disk and said distal portion comprises a distal sealing disk, and said compression mechanism for urging proximal portion and said distal portion into engagement with the wall of the vessel comprises a hollow threaded stem connecting said proximal sealing disk.

18. The multi-access perfusion cannula of claim 15, wherein said distal portion is attached to said cannula body and said proximal portion is slidable along said cannula body to engage the outside surface of the vessel.

19. The multi-access perfusion cannula of claim 15 further comprising a central passage extending through said proximal portion and said distal portion for providing access to the lumen vessel.

20. The multi-access perfusion cannula of claim 15 further comprising a hemostasis valve within said central passage, said hemostasis valve having a passage therethrough and capable of maintaining a fluidly tight seal upon introduction of an instrument through said central passage.

21. The multi-access perfusion cannula of claim 15, wherein said proximal portion comprises a proximal inflatable seal and said distal portion comprises a distal inflatable seal.

22. The multi-access perfusion cannula of claim 15, wherein said distal portion comprises an inner expandable member selectively expandable to engage the inner surface of the vessel.

23. The multi-access perfusion cannula of claim 22, wherein said inner expandable member comprises a slotted sleeve that expands radially when compressed axially to engage the inner surface of the vessel.

24. The multi-access perfusion cannula of claim 22, wherein said proximal portion comprises an outer expandable member selectively expandable to engage the outer surface of the vessel.

25. The multi-access perfusion cannula of claim 24, wherein said outer expandable member comprises a slotted sleeve that expands radially when compressed axially to engage the outer surface of the vessel.

26. A multi-access perfusion cannula comprising:

(a) an elongated tubular cannula body including a plurality of articulating access legs;

(b) a downstream directed perfusion lumen within said elongated tubular cannula body;

(c) an upstream directed access conduit within said elongated tubular cannula body configured for passage of a catheter or instrument; and (d) a sealing mechanism for sealing an insertion site of said cannula body into a vessel, having a proximal portion and a distal portion, said proximal portion covering the insertion site on an outside surface of a vessel wall by securing a distal surface of said proximal portion of said sealing mechanism against the outside surface of the vessel, said distal portion of said sealing mechanism lying intraluminally of the vessel and covering the insertion site on an inside surface of the vessel wall with a proximal surface of said distal portion of said sealing mechanism bearing against the inside surface of the vessel.

27. The multi-access perfusion cannula of claim 26 further comprising a compression mechanism for urging said proximal portion and said distal portion into engagement with the wall of the vessel.

28. The multi-access perfusion cannula of claim 27, wherein said portion comprises a proximal sealing disk and said distal portion comprises a distal sealing disk, and said compression mechanism for urging proximal portion and said distal portion into engagement with the wall of the vessel comprises a hollow threaded stem connecting said proximal sealing disk.

29. The multi-access perfusion cannula of claim 26 wherein said distal portion is attached to said cannula body and said proximal portion is slidable along said cannula body to engage the outside surface of the vessel.

30. The multi-access perfusion cannula of claim 26 further comprising a central passage extending through said proximal portion and said distal portion for providing access to the lumen vessel.

31. The multi-access perfusion cannula of claim 26 further comprising a hemostasis valve within said central passage, said hemostasis valve having a passage therethrough and capable of maintaining a fluidly tight seal upon introduction of an instrument through said central passage.

32. The multi-access perfusion cannula of claim 26, wherein said proximal portion comprises a proximal inflatable seal and said distal portion comprises a distal inflatable seal.

33. The multi-access perfusion cannula of claim 26, wherein said distal portion comprises an inner expandable member selectively expandable to engage the inner surface of the vessel.

34. The multi-access perfusion cannula of claim 33, wherein said inner expandable member comprises a slotted sleeve that expands radially when compressed axially to engage the inner surface of the vessel.

35. The multi-access perfusion cannula of claim 33, wherein said proximal portion comprises an outer expandable member selectively expandable to engage the outer surface of the vessel.

36. The multi-access perfusion cannula of claim 35, wherein said outer expandable member comprises a slotted sleeve that expands radially when compressed axially to engage the outer surface of the vessel.

* * * * *